United States Patent
Xia et al.

(10) Patent No.: US 9,557,300 B2
(45) Date of Patent: Jan. 31, 2017

(54) WIRELINE CABLE FATIGUE MONITORING USING THERMALLY-INDUCED ACOUSTIC WAVES

(71) Applicant: HALLIBURTON ENERGY SERVICES, INC., Houston, TX (US)

(72) Inventors: Hua Xia, Huffman, TX (US); Yinghui Lu, The Woodlands, TX (US); Lizheng Zhang, Humble, TX (US); John L. Maida, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/026,432

(22) PCT Filed: Nov. 12, 2014

(86) PCT No.: PCT/US2014/065226
§ 371 (c)(1),
(2) Date: Mar. 31, 2016

(87) PCT Pub. No.: WO2016/076855
PCT Pub. Date: May 19, 2016

(65) Prior Publication Data
US 2016/0327521 A1    Nov. 10, 2016

(51) Int. Cl.
*G01N 29/07* (2006.01)
*G01N 29/24* (2006.01)

(52) U.S. Cl.
CPC .......... *G01N 29/07* (2013.01); *G01N 29/2418* (2013.01); *G01N 2291/0231* (2013.01);
(Continued)

(58) Field of Classification Search
CPC ................ G01N 29/07; G01N 29/2418; G01N 2291/0231; G01N 2291/02491; G01N 2291/0258;G01N 2291/02827; G01N 29/2431; G01N 2291/2626; G01H 9/00; G01H 9/004
(Continued)

(56) References Cited

U.S. PATENT DOCUMENTS 4,979,125 A * 12/1990 Kwun .................... B65H 63/06
                                                702/35
5,804,727 A *  9/1998 Lu ............................ G01H 5/00
                                                73/159

(Continued)

OTHER PUBLICATIONS

International Search Report and Written Opinion issued in related PCT Application No. PCT/US2014/065226, mailed on Aug. 10, 2015 (9 pages).

(Continued)

*Primary Examiner* — Laura Martin
*Assistant Examiner* — Rose M Miller
(74) *Attorney, Agent, or Firm* — Scott Richardson; Baker Botts L.L.P.

(57) ABSTRACT

Systems and methods for determining whether mechanical fatigue exists in a downhole cable using thermally-induced acoustic waves are disclosed herein. A cable fatigue monitoring system includes a thermal source, one or more light sources, one or more photodetector arrays, and a computing system comprising a processor, a memory, and a cable distortion module. The cable distortion module is operable to generate acoustic waves in a cable using the thermal source, direct light from the one or more light sources toward the cable, detect light from the one or more light sources transmitted past the cable at the one or more photodetector arrays, and determine, based on the detected light transmitted past the cable, whether a change in velocity of the acoustic waves has occurred in the cable.

42 Claims, 7 Drawing Sheets

(52) U.S. Cl.
CPC ............... *G01N 2291/0258* (2013.01); *G01N 2291/02491* (2013.01); *G01N 2291/02827* (2013.01)

(58) Field of Classification Search
USPC .......................................... 73/598, 643, 597
See application file for complete search history.

(56) References Cited

U.S. PATENT DOCUMENTS

| | | |
|---|---|---|
| 6,359,446 B1 | 3/2002 | Little, Jr. |
| 6,662,660 B2 * | 12/2003 | Smith .................. B66B 7/1215 324/535 |
| 6,698,288 B2 | 3/2004 | Shirzad et al. |
| 6,838,670 B2 | 1/2005 | Lewis et al. |
| 7,080,561 B2 | 7/2006 | Bohlmann et al. |
| 7,086,285 B2 | 8/2006 | Reed |
| 7,356,444 B2 | 4/2008 | Blemel |
| 7,812,616 B2 | 10/2010 | Doyen |
| 7,884,322 B2 | 2/2011 | Sasajima et al. |
| 7,966,883 B2 | 6/2011 | Lorraine et al. |
| 8,000,572 B2 | 8/2011 | Varkey |
| 8,286,498 B1 | 10/2012 | Robertson et al. |
| 8,380,028 B2 | 2/2013 | Kojima et al. |
| 8,393,784 B2 | 3/2013 | Ringermacher et al. |
| 8,442,301 B2 | 5/2013 | Dragovich et al. |
| 2004/0099062 A1 * | 5/2004 | Smith .................. B66B 7/1215 73/801 |
| 2004/0182160 A9 * | 9/2004 | Madaras .............. G01N 29/045 73/598 |
| 2007/0131417 A1 | 6/2007 | Bolshakov et al. |
| 2010/0104060 A1 | 4/2010 | Koste et al. |
| 2012/0053852 A1 * | 3/2012 | Padilla .................. G01N 29/07 702/34 |
| 2012/0143525 A1 | 6/2012 | Chen et al. |
| 2012/0277995 A1 | 11/2012 | Hartog et al. |
| 2013/0341009 A1 | 12/2013 | Gonzalez Cancino et al. |

OTHER PUBLICATIONS

AccuScan—Diameter and Ovality Measurement Systems, http://www.betalasermike.com/index.php/en/beta-lasermike-products-en/diameter-a-ovality-en, 2 pages.

* cited by examiner

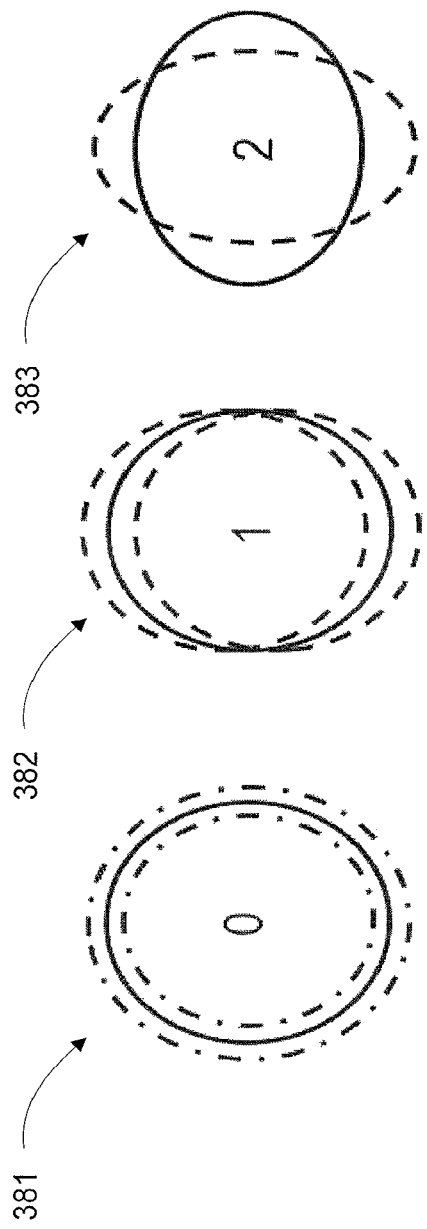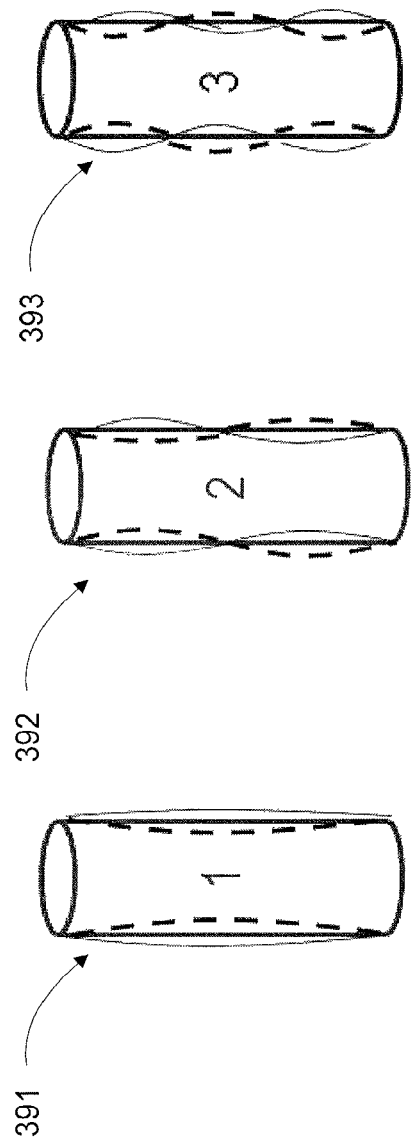
FIG. 3B
FIG. 3C

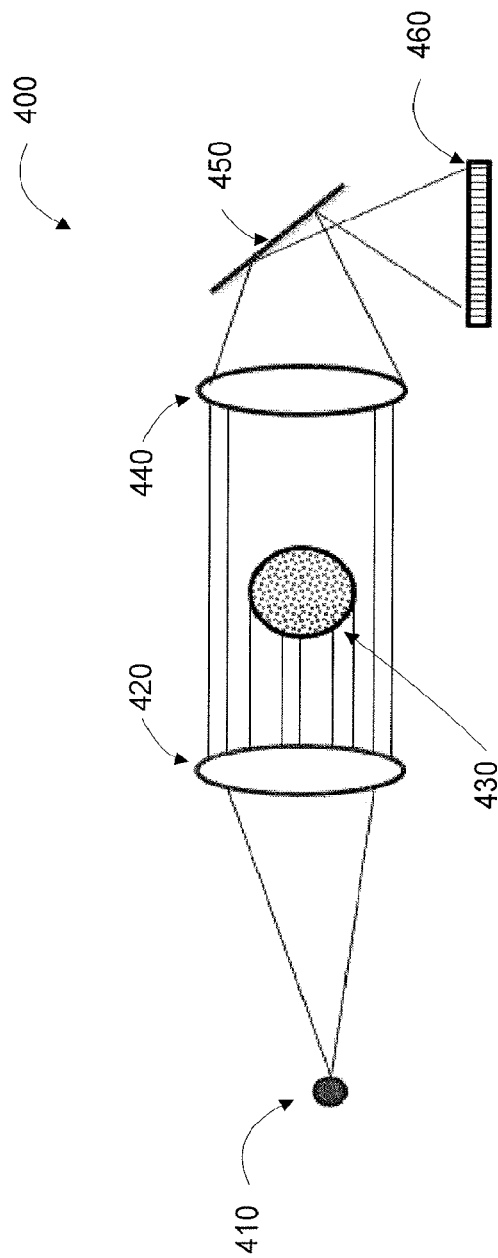
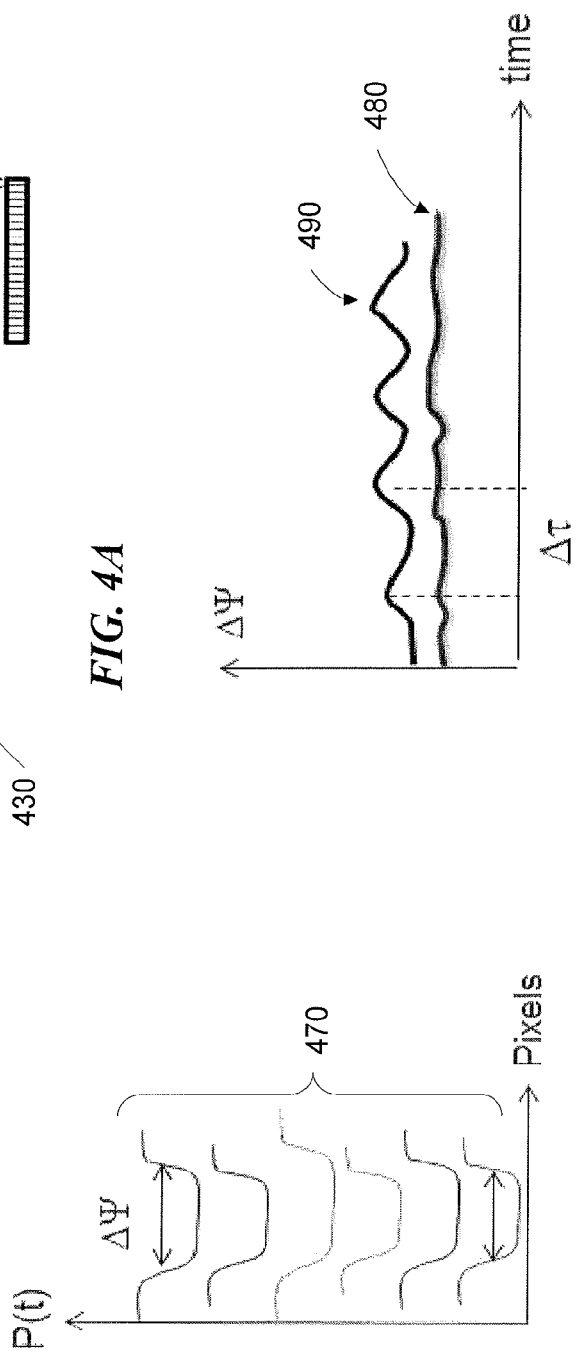
FIG. 4A
FIG. 4B
FIG. 4C

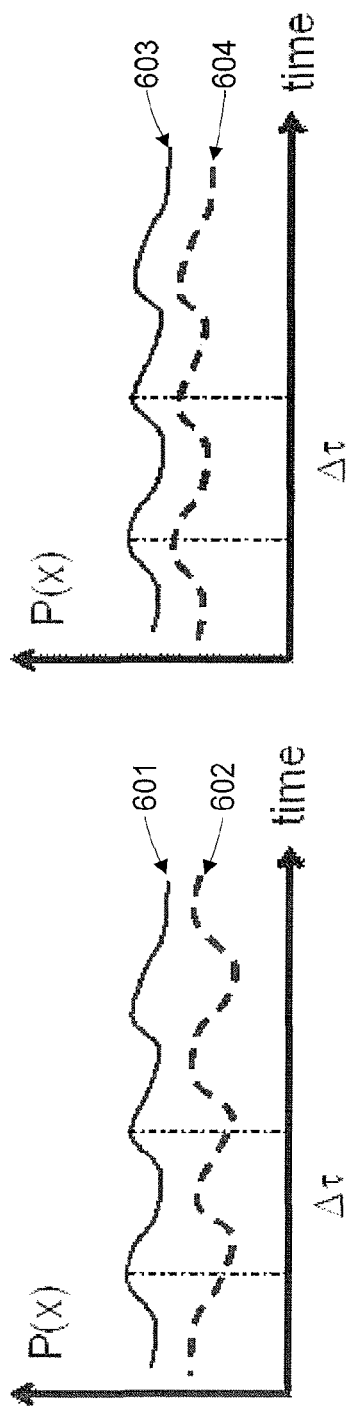
FIG. 6A
FIG. 6B
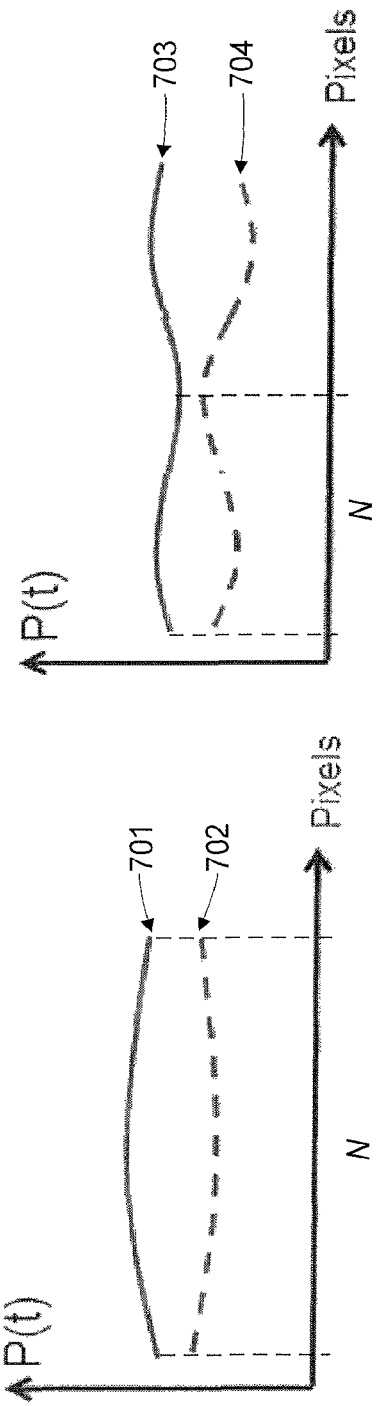
FIG. 7A
FIG. 7B

WIRELINE CABLE FATIGUE MONITORING USING THERMALLY-INDUCED ACOUSTIC WAVES

CROSS-REFERENCE TO RELATED APPLICATIONS

The present application is a U.S. National Stage Application of International Application No. PCT/US2014/065226 filed Nov. 12, 2014, which is incorporated herein by reference in its entirety for all purposes.

BACKGROUND

The present disclosure relates generally to measuring mechanical fatigue in downhole loading cables and, more particularly, to determining mechanical fatigue in polymer composite material based wireline or slickline cables using thermally-induced acoustic waves.

Hydrocarbons, such as oil and gas, are commonly obtained from subterranean formations that may be located onshore or offshore. When performing operations for removing the hydrocarbons from the subterranean formations, it may be desirable to obtain information about the formation. One method of obtaining information about the formation is the use of a wellbore logging tool coupled to a wireline or slickline system, wherein the wellbore logging tool is lowered into the wellbore using a downhole loading cable. Mechanical fatigue of the polymer composite material based cable may occur over time due to structural defects in the cable (e.g., small cracks, delaminations, or voids) and may cause logging service failure during logging operations. Current nondestructive cable inspection methods (e.g., x-ray, microwave, or gamma-ray inspection methods) may require a direct measurement of a portion of the logging tool cable, and may therefore require the cable to be relatively stationary while the measurement is taken. However, the logging tool cable may be lowered into the well during logging operations at high velocities, making stationary methods of measuring mechanical fatigue on the cable impracticable. It is therefore desirable to provide a dynamic and nondestructive inspection method to identify potential cable failure events, onset of failure modes in the cable, and degradation trends in the cable's structural strength.

BRIEF DESCRIPTION OF THE DRAWINGS

For a more complete understanding of the present disclosure and its features and advantages, reference is now made to the following description, taken in conjunction with the accompanying drawings, in which:

FIGS. 3B-3C illustrate example acoustic vibrational modes in a cable, in accordance with embodiments of the present disclosure;

FIG. 4A illustrates an example system for analyzing the fundamental circumferential vibrational mode in a cable, in accordance with embodiments of the present disclosure;

FIG. 4B illustrates example signals generated by a photodetector array at different times as a cable vibrates in a fundamental circumferential vibrational mode, in accordance with embodiments of the present disclosure;

FIG. 4C illustrates an example change in width of a cable ($\Delta\Psi$) measured over time as the cable vibrates in a fundamental circumferential vibrational mode, in accordance with embodiments of the present disclosure;

FIGS. 6A-6B illustrate example signals generated by photodetector arrays as a cable vibrates in higher order circumferential vibrational modes, in accordance with embodiments of the present disclosure;

FIGS. 7A-7B illustrate example signals generated by photodetector arrays as a cable vibrates in higher order axial vibrational modes, in accordance with embodiments of the present disclosure.

While embodiments of this disclosure have been depicted and described and are defined by reference to example embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

The present disclosure describes systems and methods for monitoring mechanical fatigue in wellbore logging tool cables by measuring velocity of thermally-induced acoustic waves propagating in a wireline or slickline cable in a wellbore. This cable may be based on polymer composite materials, coiled tubes, metal micro tubes and fiber optic hybrid helix structure, and/or metal wires. The distortions caused by the acoustic waves down the cable may enable the detection of the speed of the waves and nodal patterns using a laser-based displacement system. In particular embodiments, light may be cylindrically-focused onto a section of the cable to measure displacements in the cable caused by the acoustic waves (which are generated by the thermal source). Scattered light may then be analyzed by one or more photodetector arrays (e.g., charge-coupled device (CCD), complementary metal-oxide semiconductor (CMOS), or position sensitive detector (PSD)). In certain embodiments, the effective speed of the sound may be analyzed from axial and circumferential nodal patterns of distortion measured in the cable. Under a constant thermal source causing the acoustic excitation, deviations in either the speed of the acoustic waves or in the nodal pattern observed in the cable may be used to correlate directly with the cable's elastic modulus degradation, or indirectly with the cable's mechanical fatigue.

To facilitate a better understanding of the present disclosure, the following examples of certain embodiments are given. In no way should the following examples be read to limit, or define, the scope of the disclosure. Embodiments of the present disclosure and its advantages are best understood by referring to FIGS. 1 through 8, where like numbers are used to indicate like and corresponding parts.

Figure 1:
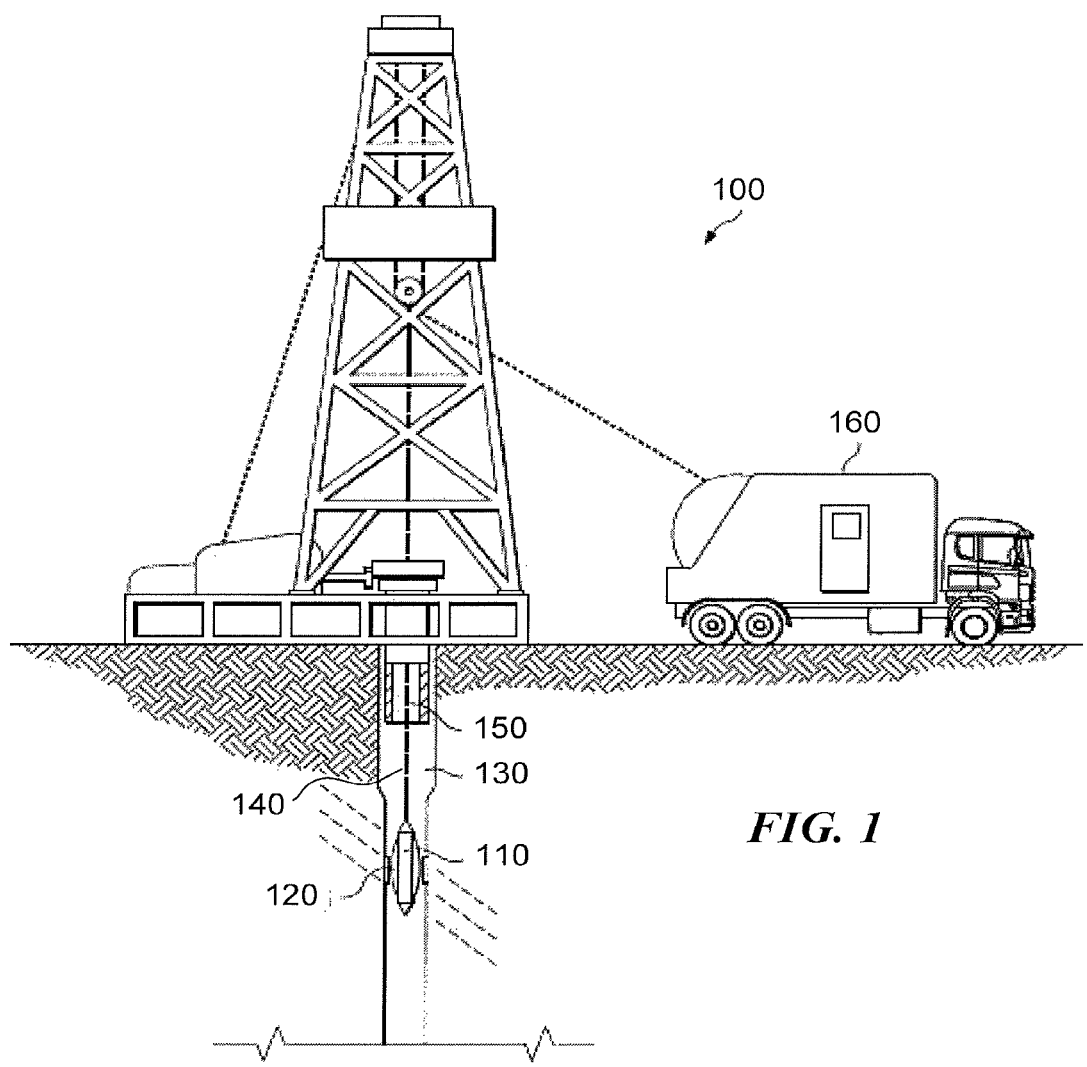
FIG. 1 illustrates an example downhole logging tool system used in a hydrocarbon drilling environment, in accordance with embodiments of the present disclosure.

FIG. 1 illustrates an example downhole logging tool system 100 used in a hydrocarbon drilling environment, in accordance with embodiments of the present disclosure. Operations in a wellbore may be conducted using wireline system 110 when some or all of a drill string has been removed from the wellbore. Wireline system 110 may include one or more logging tools 120 that may be suspended into wellbore 130 by cable 140 (e.g., wireline, slickline, or coiled tubing). Logging tool 120 may be communicatively coupled to cable 140, which may contain conductors for transporting power to wireline system 110 and signals from logging tool 120 to logging facility 160. However, cable 140 may alternatively lack a conductor, as is often the case using slickline or coiled tubing. Cable distortion measurement system 150 may include components (e.g., heaters, lasers, photodetectors, and computing facilities) operable to measure distortions in cable 140 using thermally-induced acoustic waves, as described further below with respect to FIGS. 3-7. Cable distortion measurement system 150 may be communicably coupled to logging facility 160 using any suitable means, such as through cable 140 or through a wireless connection. Logging facility 160 (shown in FIG. 1 as a truck, although it may be any other structure) may collect measurements from logging tool 126 or cable distortion measurement system 150, and may include computing facilities for controlling, processing, or storing the measurements communicated thereto. The computing facilities may be communicatively coupled to the components of downhole logging system 100 through any suitable means. An example computing facility is described further below with reference to FIG. 2.

Modifications, additions, or omissions may be made to FIG. 1 without departing from the scope of the present disclosure. For example, FIG. 1 illustrates components of downhole logging system 100 in a particular configuration. However, any suitable configuration of components for logging a wellbore may be used. Furthermore, fewer components or additional components beyond those illustrated may be included in downhole logging system 100 without departing from the scope of the present disclosure.

Figure 2:
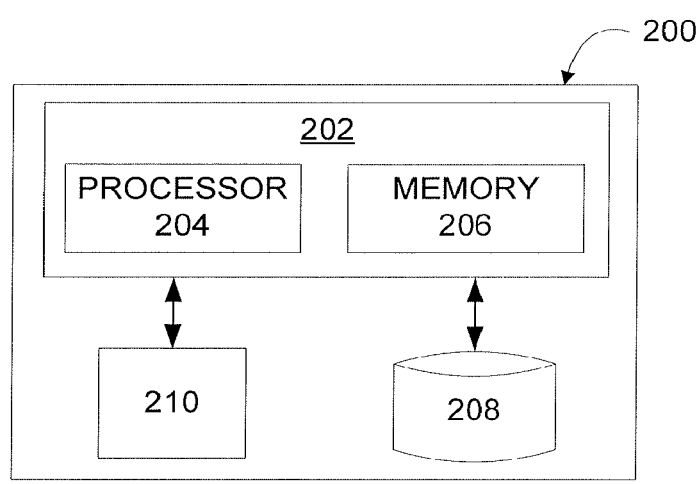
FIG. 2 illustrates a block diagram of an exemplary computing system for use in a downhole tool logging system, in accordance with embodiments of the present disclosure.

FIG. 2 illustrates a block diagram of an exemplary computing system 200 for use in a downhole logging tool system, in accordance with embodiments of the present disclosure. Computing system 200 or components thereof can be located at the surface (e.g., in logging facility 160), downhole (e.g., in cable distortion measurement system 150), or some combination of both locations (e.g., certain components may be disposed at the surface while certain other components may be disposed downhole, with the surface components being communicatively coupled to the downhole components). Computing system 200 may be configured to measure potential cable fatigue by measuring changes in the velocity of thermally-induced acoustic waves propagating in the cable, in accordance with the teachings of the present disclosure. For example, computing system 200 may be configured to perform the steps of the methods described below with respect to FIG. 8.

Computing system 200 may include cable distortion module 202. Cable distortion module 202 may include any suitable components. For example, in some embodiments, cable distortion module 202 may include processor 204. Processor 204 may include, for example a microprocessor, microcontroller, digital signal processor (DSP), application specific integrated circuit (ASIC), or any other digital or analog circuitry configured to interpret and/or execute program instructions and/or process data. In some embodiments, processor 204 may be communicatively coupled to memory 206. Processor 204 may be configured to interpret and/or execute program instructions or other data retrieved and stored in memory 206. Program instructions or other data may constitute portions of software 208 for carrying out one or more methods described herein. Memory 206 may include any system, device, or apparatus configured to hold and/or house one or more memory modules; for example, memory 206 may include read-only memory, random access memory, solid state memory, or disk-based memory. Each memory module may include any system, device or apparatus configured to retain program instructions and/or data for a period of time (e.g., computer-readable non-transitory media). For example, instructions from software 208 may be retrieved and stored in memory 206 for execution by processor 204. Cable distortion module 202 may be communicatively coupled to one or more displays 210 (e.g., located in logging facilities 160 of FIG. 1) such that information processed by wellbore ranging module 202 may be conveyed to operators of the downhole logging system. For example, cable distortion module 202 may convey measurements indicating determined cable fatigue characteristics to display 210.

Modifications, additions, or omissions may be made to FIG. 2 without departing from the scope of the present disclosure. For example, FIG. 2 shows a particular configuration of components of computing system 200. However, any suitable configurations of components may be used. For example, components of computing system 200 may be implemented either as physical or logical components. Furthermore, in some embodiments, functionality associated with components of computing system 200 may be implemented in special purpose circuits or components. In other embodiments, functionality associated with components of computing system 200 may be implemented in configurable general purpose circuit or components. For example, components of computing system 200 may be implemented by configured computer program instructions.

Figure 3A:
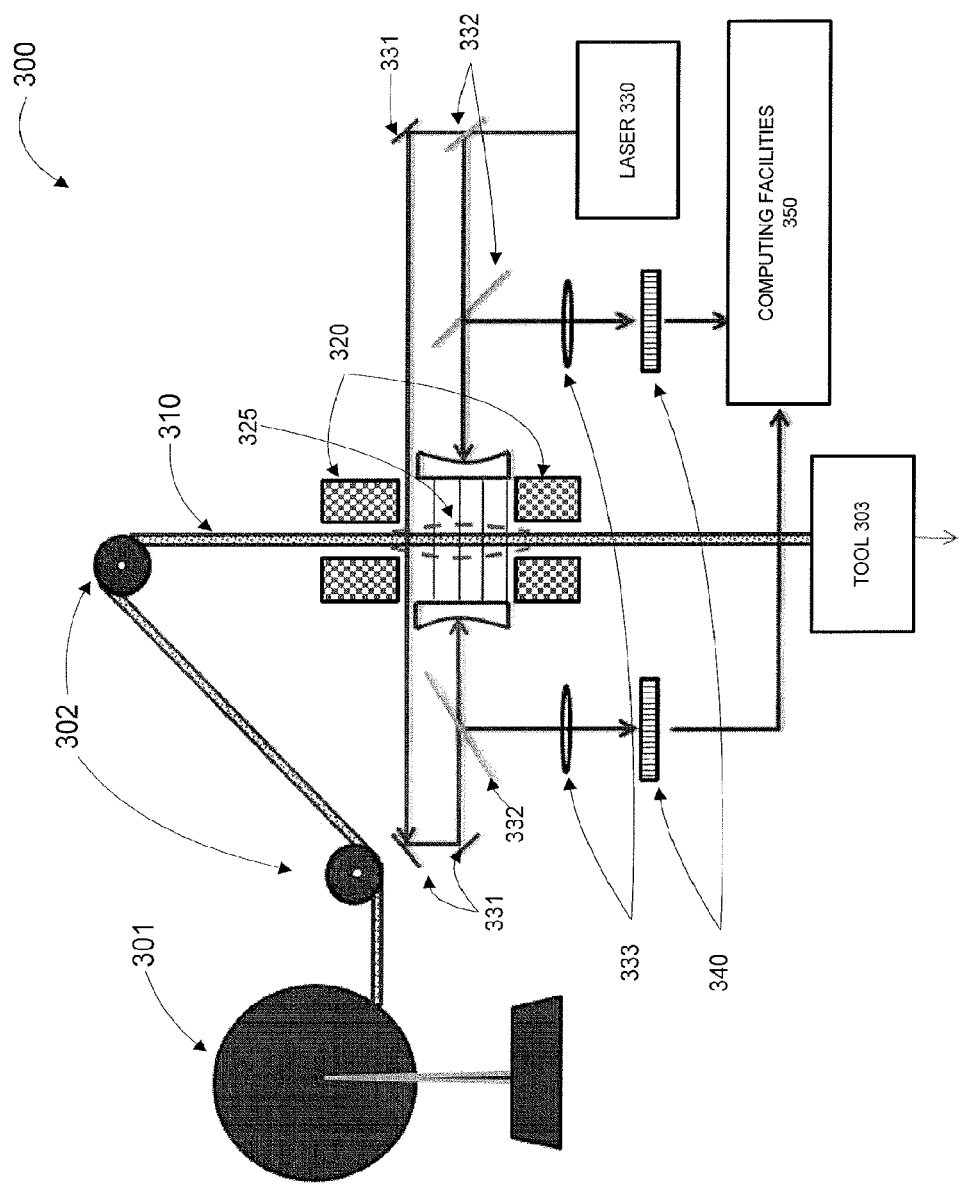
FIG. 3A illustrates an example system for measuring distortions in a cable caused by thermally-induced acoustic vibrations, in accordance with embodiments of the present disclosure.

FIG. 3A illustrates an example system 300 for measuring distortions in a cable 310 caused by thermally-induced acoustic vibrations, in accordance with embodiments of the present disclosure. System 300 comprises a cable spool 301 and one or more pulleys 302 that assist in lowering logging tool 303 down into a wellbore using cable 310 at a certain velocity. Cable spool 301 and pulleys 302 may be located in any suitable location, such as at a surface of a wellbore. For example, cable spool 301 may be located inside logging facilities such as the logging facilities 160 of FIG. 1 (i.e., the truck illustrated in FIG. 1). Pulleys 302 may be similarly located in logging facilities, or in a rig as shown in FIG. 1 or downhole. Logging tool 303 may be any suitable tool used for logging a formation, such as logging tool 120 of FIG. 1.

System 300 further comprises one or more acoustic-exciting thermal sources 320 located in close proximity to cable 310. For example, acoustic-exciting thermal sources 320 may be placed on either side of a cable analysis area 325, as shown in FIG. 3. Example acoustic-exciting thermal sources may include induction heaters, flash light beams, or any pulsed thermal energy emitter. Acoustic-exciting thermal sources 320 may heat portions of cable 310 in cable analysis area 325 as it is lowered, inducing an acoustic wave that propagates along cable 310. Under the transient perturbations caused by the acoustic waves, circumferential or axial modes may be excited (such as those illustrated in FIGS. 3B and 3C, and described further below). Acoustic-exciting thermal sources 320 may be modulated over a range of carrier frequencies in some embodiments. The time of arrival of the induced acoustic waves propagating along cable 310 may be used to determine a propagation velocity of the acoustic waves and the manner in which that the phase velocity varies with the carrier frequency. By determining the propagation velocity of the acoustic waves, information regarding the mechanical strength or fatigue status of cable 310 may be determined, as described further below. In addition, attenuation of the acoustic waves as a function of frequency may be measured and used to determine an amount of degradation in cable 310, as described further below.

A symmetrical optical signal detection system such as the one illustrated in FIG. 3A may be used to analyze mechanical fatigue in cable 310. In particular, as acoustic-exciting thermal sources 320 heat cable 310 and thus generate acoustic waves that propagate through cable 310, a beam of light generated by laser 330 may be directed toward a cable analysis area 325 of cable 310 by one or more mirrors 331, one or more dichroic filters 332, and/or one or more lenses 333 as shown in FIG. 3A. The light directed toward cable 310 may be transmitted past cable 310 or may be reflected by cable 310, and then directed toward one or more photodetector arrays 340. Photodetector arrays 340 may generate signals associated with the received light scattered by cable 310, and send those signals to computing facilities 350 for analysis. Computing facilities may be similar to computing system 200 of FIG. 2, and may be located uphole (e.g., in logging facilities 160 of FIG. 1), downhole (e.g., in logging tool 120 of FIG. 1), or in a combination thereof. Example embodiments of signal detection systems for analyzing mechanical fatigue in cable 310 are described further below with respect to FIGS. 4-8.

FIGS. 3B-3C illustrate example acoustic vibrational modes in a cable, in accordance with embodiments of the present disclosure, in accordance with embodiments of the present disclosure. In particular FIG. 3B illustrates example circumferential acoustic modes 381-383 (i.e., those that affect the cable's circumference along a length of the cable), and FIG. 3C illustrates example axial acoustic nodes 391-393 (i.e., those that affect the cable along the length of the cable). Circumferential vibrational mode 381 illustrates the fundamental mode (or the 0 order mode), which corresponds to a diameter variation as shown with dotted lines. Circumferential vibrational modes 382-383 illustrate the first order and the second order modes, respectively, and reflect shape variation and vibration as shown with dotted lines. The axial modes 391-393 may be described by flexural vibration similar to a standing wave across a sectional cable length. For a guided acoustic wave propagating along a cable, the time of arrival of the wave at each position along the cable may provide a measure of the group velocity of the wave. In addition, the wavelength may provide a measure of phase velocity of the wave. In some embodiments, the group velocity dispersion of the acoustic waves may be measured by causing successive narrow-band acoustic pulses of varying carrier frequency to be propagated along the cable, and observing the variation of transit time as a function of carrier frequency.

Modifications, additions, or omissions may be made to FIGS. 3A-3C without departing from the scope of the present disclosure. For example, FIG. 3A illustrates components of system 300 in a particular configuration. However, any suitable configuration of components for measuring distortions in a downhole cable according to the present disclosure may be used. Furthermore, fewer components or additional components beyond those illustrated in FIG. 3A may be included in system 300 without departing from the scope of the present disclosure. As another example, although particular modes are shown in FIGS. 3B-3C, additional acoustic modes may be analyzed using the teachings of the present disclosure.

FIG. 4A illustrates an example system 400 for analyzing the fundamental circumferential vibrational mode in a cable, in accordance with embodiments of the present disclosure. In particular embodiments, the fundamental circumferential vibrational mode may be the dominant mode (i.e., the mode with the strongest magnitude). System 400 includes a light source 410 that is first collimated by one or more lenses 420 and then directed toward cable 430 in collimated beams. Light from the collimated beams that passes cable 430 without deflection may then pass through lens 440 and be directed toward photodetector array 460 by mirror 450. Accordingly, a shadow having the approximate width of cable 430 may be cast onto photodetector array 460.

FIG. 4B illustrates example signals 470 generated by photodetector array 460 at different times as cable 430 vibrates in a fundamental circumferential vibrational mode, in accordance with embodiments of the present disclosure. Referring to FIG. 4B, P(t) indicates the signal magnitude on photodetector array 460 across its pixels and $\Delta\Psi$ indicates the width of the shadow cast on photodetector array 460 (i.e., the signal is lower over the portion of photodetector array 460 where the shadow is cast). In the fundamental vibrational mode, the diameter of cable 430 will change as indicated by mode 381 of FIG. 3B. Accordingly, signals 470 will have varied $\Delta\Psi$ values when measured at different times, as shown.

FIG. 4C illustrates an example change in width of cable 430 ($\Delta\Psi$) measured over time as cable 430 vibrates in a fundamental circumferential vibrational mode, in accordance with embodiments of the present disclosure. Line 480 represents a an example baseline measurement of $\Delta\Psi$ over time with no fundamental vibrational mode present, while line 490 represents an example measurement of $\Delta\Psi$ over time with a fundamental vibrational mode present. Because of the harmonic characteristic of this fundamental vibrational mode, a fundamental acoustic wavelength may be determined. In particular, the time difference, $\Delta\tau$, may be associated with time delay or propagation time for one wavelength distance, and therefore directly related to the velocity of the acoustic waves in cable 430. Changes in $\Delta\tau$ (i.e., in the velocity of the acoustic waves), may therefore indicate changes in the elastic modulus of cable 430, which may also indicate that mechanical fatigue exists in cable 430.

Although FIG. 4A illustrates a single-axis system (i.e., light is directed toward cable 430 in a single axis) for analyzing vibrational modes in a cable, it will be understood that a multiple-axis system is contemplated in the present disclosure. For example, two-axis system may comprise an additional optical path perpendicular to the single-axis path illustrated in FIG. 4A. This may include a second light path (e.g., using additional mirrors and/or lenses) directing light from light source 410 toward cable 430 in the vertical axis in addition to the horizontal-axis system illustrated in FIG. 4A. Furthermore, in certain embodiments, a two-axis system with light axes at 45° offset along cable 430 may be implemented to observe higher order vibrational modes in cable 430.

Modifications, additions, or omissions may be made to FIGS. 4A-4C without departing from the scope of the present disclosure. For example, FIG. 4A illustrates components of system 400 in a particular configuration. However, any suitable configuration of components for measuring fundamental mode distortions in a downhole cable according to the present disclosure may be used. Furthermore, fewer components or additional components beyond those illustrated in FIG. 4A may be included in system 400 without departing from the scope of the present disclosure. For example, a two-axis configuration as described above may be used.

Figure 5A:
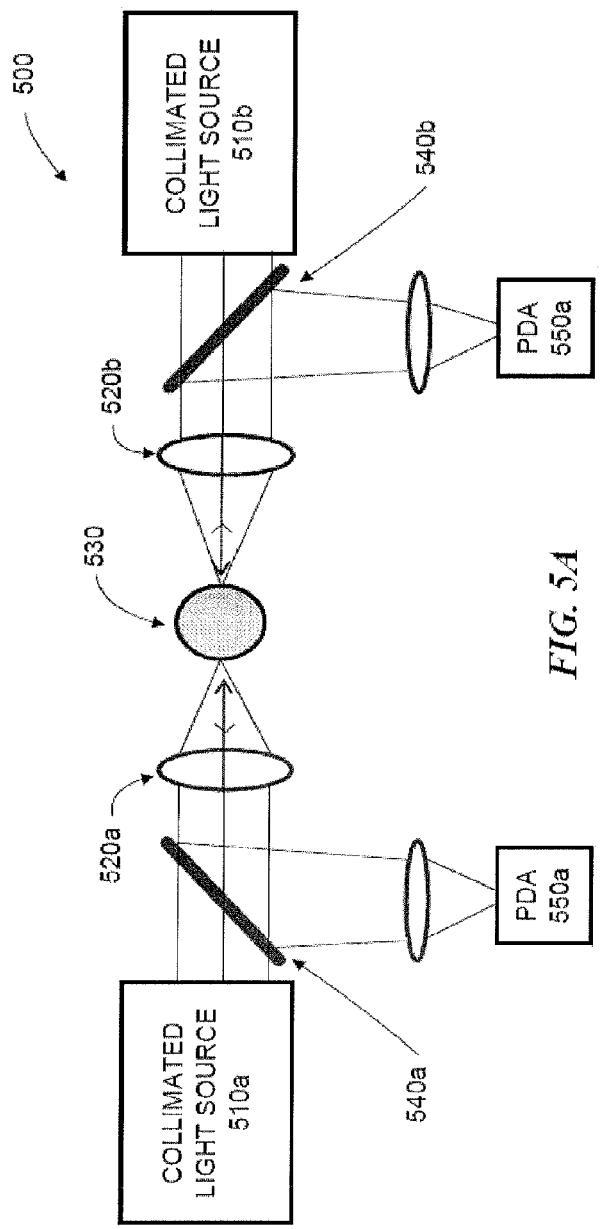
FIGS. 5A-5B illustrates an example system for analyzing higher order circumferential and axial vibrational modes in a cable, in accordance with embodiments of the present disclosure.
Figure 5B:
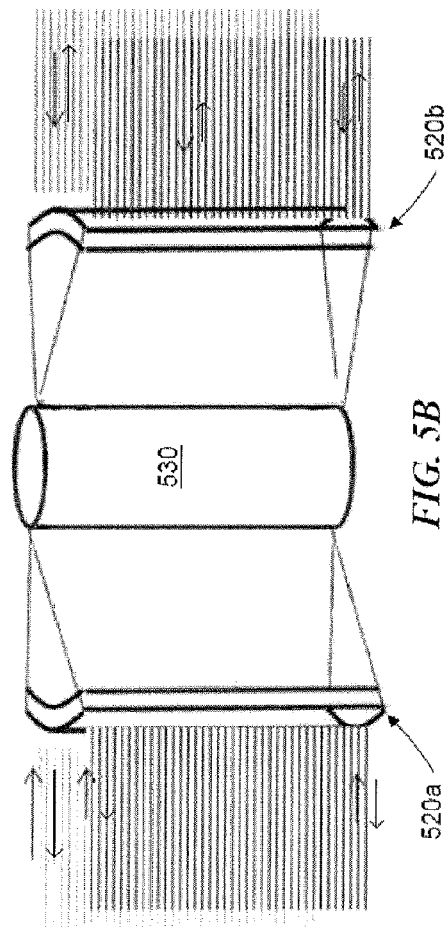

FIGS. 5A-5B illustrates an example system 500 for analyzing higher order circumferential and axial vibrational modes in a cable, in accordance with embodiments of the present disclosure. In particular, FIG. 5A illustrates a cross-sectional view of system 500 looking down cable 530, and FIG. 5B illustrates a side perspective view of system 500 looking down a length of cable 530. System 500 includes two collimated light sources 510 that are focused onto cable 530 by one or more lenses 520. Collimated light sources 510 may include a non-collimated light and a lens configured to collimate the light, similar to light source 410 and lens 420 of FIG. 4A. In particular embodiments, the collimated light sources 510 may be configured such that they are on opposite sides of cable 530. The light focused onto cable 530 may be reflected back from cable 530, through lenses 520, and then directed toward photodetector arrays 550 by 50/50 dichroic filters 540, as shown. Lenses may be cylindrical lenses that focus the collimated light from sources 510 onto cable 530 along a length of cable 530 as shown in FIG. 5B. As cable 530 vibrates in one or more higher order vibrational modes (i.e., not the fundamental modes), it may cause changes in the reflections from cable 530 sent to photodetector arrays 550. Example signals associated with the higher order vibrational modes are described below with respect to FIGS. 6-7.

Although FIGS. 5A-5B illustrate a single-axis system (i.e., light is directed toward cable 530 in a single axis) for analyzing vibrational modes in a cable, it will be understood that a multiple-axis system is contemplated in the present disclosure. For example, a two-axis system may comprise an additional optical path perpendicular to the single-axis path illustrated in FIGS. 5A-5B. This may include a second light path (e.g., using additional mirrors and/or lenses) directing light from light sources 510 toward cable 530 in the vertical axis in addition to the horizontal-axis system illustrated in FIG. 5A. Furthermore, in certain embodiments, a two-axis system with light axes at 45° offset along cable 530 may be implemented to observe higher order vibrational modes in cable 530.

Modifications, additions, or omissions may be made to FIGS. 5A-5B without departing from the scope of the present disclosure. For example, FIGS. 5A-5B illustrates components of system 500 in a particular configuration, namely a single-axis configuration. However, any suitable configuration of components for measuring distortions in a downhole cable according to the present disclosure may be used. Furthermore, fewer components or additional components beyond those illustrated in FIGS. 5A-5B may be included in system 500 without departing from the scope of the present disclosure. For example, a two-axis configuration as described above may be used.

FIGS. 6A-6B illustrate example signals 601-604 generated by photodetector arrays 550 of FIGS. 5A-5B as cable 530 vibrates in higher order circumferential vibrational modes, in accordance with embodiments of the present disclosure. In particular, FIG. 6A illustrates signals 601-602 associated with a first order circumferential vibrational mode similar to mode 382 of FIG. 3B, while FIG. 6B illustrates signals 603-604 associated with a second order circumferential vibrational mode similar to mode 383 of FIG. 3B. FIGS. 6A-6B illustrate a signal intensity generated by a photodetector array 550 associated with light reflected by cable 530 at a particular point x along cable 530 over time.

In a first order circumferential vibrational mode, the cable may shift back and forth as shown by mode 382 of FIG. 3B. Referring to FIG. 5A, the shifting may occur in the left-right direction, which may generate signals 601 and 602 of FIG. 6A having a 180° phase shift. This is because cable 530 is moving first toward and then away from the focused beam of light as it vibrates for one side of FIG. 5A and vice-versa for the other side, which causes opposite reflections to be made back toward the two photodetector arrays 550. In particular embodiments, the time interval, $\Delta\tau$, between the peak and valleys of signals 601-602 may be directly related to the velocity of the acoustic waves in cable 530, and thus the elastic modulus of the cable. Changes in $\Delta\tau$ (i.e., in the velocity of the acoustic waves), may therefore indicate changes in the elastic modulus of cable 530. Thus, changes in $\Delta\tau$ may indicate that mechanical fatigue exists in cable 530.

In a second order circumferential vibrational mode, the cable may change in an elliptical fashion as shown by mode 383 of FIG. 3B. Referring to FIG. 5A, the elliptical change may first occur in the left-right direction and then in the up-down direction, which may generate signals 603 and 604 of FIG. 6B having a 0° phase difference. This is because the edges of cable 530 move toward and away from both sides simultaneously (i.e., toward when the cable is elliptically elongated in the left-right direction with respect to FIG. 5A, and away when the cable is elliptically elongated in the up-down direction), causing the reflections from cable 530 back to photodetector arrays 550 to be similar. As with the first mode signals, the time interval, $\Delta\tau$, between the peak and valleys of signals 603-604 may be used to calculate the velocity of the acoustic waves in cable 530, and thus used to determine whether mechanical fatigue exists in cable 530.

FIGS. 7A-7B illustrate example signals 701-704 generated by photodetector arrays 550 of FIGS. 5A-5B as cable 530 vibrates in higher order axial vibrational modes, in accordance with embodiments of the present disclosure. In particular, FIG. 7A illustrates signals 701-702 associated with a first order axial vibrational mode similar to mode 391 of FIG. 3C, while FIG. 7B illustrates signals 703-704 associated with a second order axial vibrational mode similar to mode 392 of FIG. 3C. FIGS. 7A-7B illustrate a signal intensity generated by a photodetector array at a particular point in time t over the cross section of the photodetector array.

In a first order axial vibrational mode, the cable may vibrate back and forth as shown by mode 391 of FIG. 3C. Referring to FIG. 5B, this same pattern of change may be seen in cable 530, which may generate signals 701 and 702 of FIG. 7A having a 180° phase shift. Similar to the first order circumferential mode, this is caused by cable 530 is moving first toward and then away from the focused beam of light as it vibrates for one side of FIG. 5B and vice-versa for the other side, which in turn causes opposite reflections to be made back toward the two photodetector arrays 550. In a second order axial vibrational mode, the cable may vibrate as shown mode 392 of FIG. 3C. Referring to FIG. 5B, this same pattern of change may be seen in cable 530, which may generate signals 703 and 704 of FIG. 7B also having a 180° phase shift.

If the total pixel number of the photodetector array is k, corresponding to a sectional length of L, the pixel number, N, between the peak and valley of signals 701-704 will correspond to an acoustic wavelength which may be determined by Equation (1):

$$\lambda = \frac{L*N}{k}$$

If the carrier frequency, f, is narrow-band (e.g., 5-25 kHz or 10-20 kHz), for example, the phase velocity of the acoustic wave may then be approximately determined by Equation (2)

$$\upsilon \approx \lambda * f$$

where the phase velocity may be expressed as Equation (3)

$$\upsilon \approx \sqrt{E/\rho}$$

where E is effective elastic modulus or Young modulus of cable 530, and ρ is the effective density of cable 530.

In particular embodiments, measurements of the phase velocity and wave attenuation as a function of carrier frequency may enable a close correlation with the mechanical strength of a composite cable. In addition, and more importantly, long-term degradation trends may be observed. For a given single frequency, however, ultrasonic waves can also generate harmonics through a fatigued material because the nonlinearity of stress-strain relationship becomes more perceivable with larger higher order elastic constants due to the fatigue. The nonlinearity of the stress-strain relationship may be connected with third-order or higher terms in the strain-energy function. If we consider the third-order term only, the one-dimensional plane longitudinal wave equation becomes Equation 4:

$$\frac{\partial^2 y}{\partial x^2} = \upsilon^2 \left(1 - \beta \frac{\partial u}{\partial x}\right)\frac{\partial^2 u}{\partial x^2}$$

where u is the displacement and β is the nonlinear parameter proportional to the magnitude of nonlinearity. For a single frequency input, $u_0 \cos(\omega t)$, the solution of Equation (4) can be written as Equation 5:

$$u(x, t) = \frac{1}{8}\beta k^2 u_0^2 x + u_0 \cos(kx - \omega t) - \frac{1}{8}\beta k^2 u_0^2 x \cos(2(kx - \omega t)) + \dots$$

Accordingly, β may be estimated by measuring the amplitudes of second or higher harmonics, which may allow for an inference of mechanical fatigue on the cable.

Figure 8:
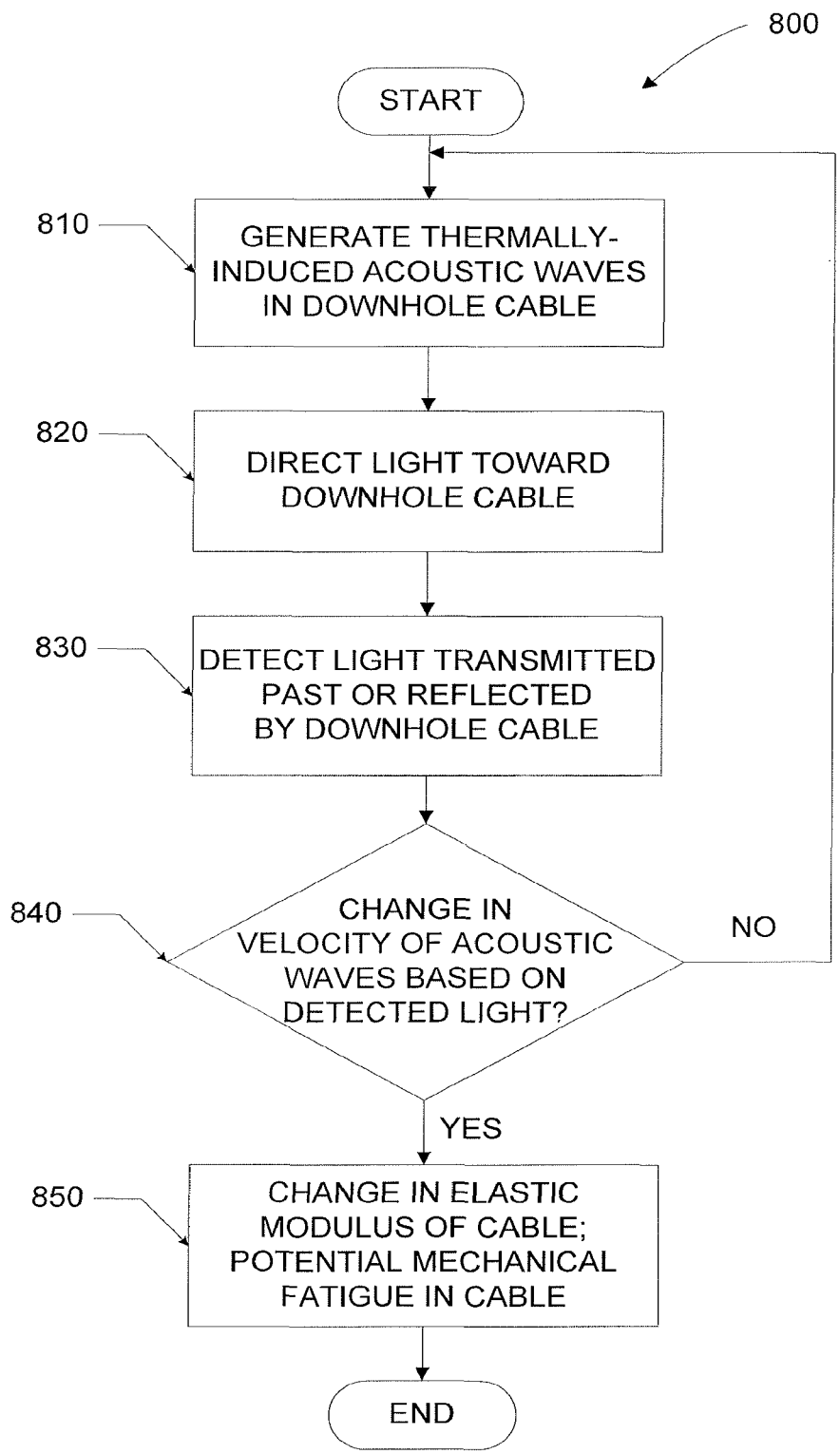
FIG. 8 illustrates an example method for determining mechanical fatigue in a cable, in accordance with embodiments of the present disclosure.

FIG. 8 illustrates an example method 800 for determining mechanical fatigue in a cable, in accordance with embodiments of the present disclosure. Method 800 may begin at step 810, where thermally-induced acoustic waves are generated in a cable. The cable may be a wireline or slickline cable lowered into a wellbore in particular embodiments, similar to cable 310 of FIG. 3A. The acoustic waves may be generated by thermal sources such as induction heaters, flash light beam, or any pulsed thermal energy emitter that are located proximate to the cable as it is lowered. At step 820, light is sent toward the cable. For example, light from a light source may directed toward the cable, as shown in FIGS. 4A and 5A-5B. The light directed toward the cable may be collimated (e.g., to detect light that transmits past the cable), or may be focused onto the cable (e.g., to detect the light that is reflected by the cable).

At step 830, light transmitted past or reflected by the cable is detected. The light may be detected at one or more photodetector arrays in certain embodiments. For example, symmetrical photodetector array arrangement as shown in FIGS. 5A-5B may be implemented. Light transmitted past the cable may be used to determine characteristics (e.g., transit time or wavelength) of a fundamental circumferential vibrational mode in the cable, as discussed above with respect to FIGS. 4A-4C. Light reflected by the cable may be used to determine higher order circumferential or axial vibrational modes in the cable, as discussed above with respect to FIGS. 5A-5B.

At step 840, changes in the velocities of the acoustic waves propagating in the cable are determined. The velocity change may be in the propagation velocity of the acoustic waves or the phase velocity of the acoustic waves. Because the velocity of the acoustic waves in the cable is directly related to the elastic modulus of the cable, a change in the acoustic wave velocity may indicate a change in the elastic modulus and therefore, potential cable fatigue at step 850. In some embodiments, an estimated velocity of the acoustic waves may be determined, and an elastic modulus of the cable may be determined using the velocity of the acoustic waves. If no change in velocity is determined, then the method returns to step 810 and repeats. In some embodiments, alerts may be generated if a change in velocity is determined at step 840. For example, an alert may be generated to indicate the potential mechanical fatigue in the cable to an operator of the downhole logging system.

Modifications, additions, or omissions may be made to method 800 without departing from the scope of the present disclosure. For example, the order of the steps may be performed in a different manner than that described and some steps may be performed at the same time. Additionally, each individual step may include additional steps without departing from the scope of the present disclosure. Furthermore, method 800 may be performed using a multiple-axis system with certain steps being performed simultaneously for each axis, or method 800 may be modified to accommodate separate axes of measurement.

To provide illustrations of one or more embodiments of the present disclosure, the following examples are provided. In one embodiment, a cable fatigue monitoring system comprises a thermal source, one or more light sources, one or more photodetector arrays, and a computing system comprising a processor, a memory, and a cable distortion module. The cable distortion module is operable to generate acoustic waves in a cable using the thermal source, direct light from the one or more light sources toward the cable, detect light from the one or more light sources transmitted past the cable at the one or more photodetector arrays, and determine, based on the detected light transmitted past the cable, whether a change in velocity of the acoustic waves has occurred in the cable.

In one or more aspects of the disclosed system, the acoustic waves comprise one or more circumferential vibrational modes.

In one or more aspects of the disclosed system, the cable distortion module operable to determine whether a change in velocity of the acoustic waves has occurred in the cable is further operable to determine whether a change in a propagation velocity of the acoustic waves has occurred.

In one or more aspects of the disclosed system, the cable distortion module operable to determine whether a change in velocity of the acoustic waves has occurred in the cable is further operable to determine a propagation time for a wavelength of the acoustic waves.

In one or more aspects of the disclosed system, the cable distortion module operable to direct light from the one or more light sources toward the cable is further operable to collimate the light from the one or more light sources and direct the collimated light toward the cable.

In one or more aspects of the disclosed system, the cable distortion module is further operable to detect light from the one or more light sources reflected by the cable at the one or more photodetector arrays, and determine, based on the detected light reflected by the cable, whether a change in velocity of the acoustic waves has occurred in the cable. In one or more aspects of the disclosed system, the acoustic waves comprise one or more axial vibrational modes.

In one or more aspects of the disclosed system, the cable distortion module operable to determine whether a change in velocity of the acoustic waves has occurred in the cable is further operable to determine a phase velocity of the acoustic waves and determine an elastic modulus of the cable using the determined phase velocity.

In one or more aspects of the disclosed system, the cable distortion module operable to determine whether a change in velocity of the acoustic waves has occurred in the cable is further operable to determine whether a change in a phase velocity of the acoustic waves has occurred.

In one or more aspects of the disclosed system, the cable distortion module operable to determine whether a change in velocity of the acoustic waves has occurred in the cable is further operable to determine a wavelength of the acoustic waves.

In one or more aspects of the disclosed system, the cable distortion module operable to direct light from the one or more light sources toward the cable is further operable to focus the light from the one or more light sources onto the cable.

In another embodiment, a method comprises generating acoustic waves in a cable using a thermal source, directing light from one or more light sources toward the cable, detecting light from the one or more light sources transmitted past the cable at one or more photodetector arrays, and determining, based on the detected light transmitted past the cable, that a change in velocity of the acoustic waves has occurred in the cable.

In one or more aspects of the disclosed method, the acoustic waves comprise one or more circumferential vibrational modes.

In one or more aspects of the disclosed method, the method further comprises detecting light from the one or more light sources reflected by the cable at the one or more photodetector arrays, and determining, based on the detected light reflected by the cable, that a change in velocity of the acoustic waves has occurred in the cable.

In one or more aspects of the disclosed method, determining whether a change in velocity of the acoustic waves has occurred in the cable further comprises determining whether a change in a propagation velocity of the acoustic waves has occurred.

In one or more aspects of the disclosed method, determining whether a change in velocity of the acoustic waves has occurred in the cable further comprises determining a propagation time for a wavelength of the acoustic waves.

In one or more aspects of the disclosed method, directing light from the one or more light sources toward the cable further comprises collimating the light from the one or more light sources and directing the collimated light toward the cable.

In one or more aspects of the disclosed method, determining whether a change in velocity of the acoustic waves has occurred in the cable further comprises determining a phase velocity of the acoustic waves and determining an elastic modulus of the cable using the determined phase velocity.

In one or more aspects of the disclosed method, the acoustic waves comprise one or more axial vibrational modes.

In one or more aspects of the disclosed method, determining whether a change in velocity of the acoustic waves has occurred in the cable further comprises determining whether a change in a phase velocity of the acoustic waves has occurred.

In one or more aspects of the disclosed method, determining whether a change in velocity of the acoustic waves has occurred in the cable further comprises determining a wavelength of the acoustic waves.

In one or more aspects of the disclosed method, directing light from the one or more light sources toward the cable further comprises focusing the light from the one or more light sources onto the cable.

In another embodiment, a computer-readable medium comprises instructions that, when executed by a processor, cause the processor to generate acoustic waves in a cable using a thermal source, direct light from one or more light sources toward a cable, detect light from the one or more light sources transmitted past the cable at one or more photodetector arrays, and determine, based on the detected light transmitted past the cable, whether a change in velocity of the acoustic waves has occurred in the cable.

In one or more aspects of the disclosed computer-readable medium, the acoustic waves comprise one or more circumferential vibrational modes.

In one or more aspects of the disclosed computer-readable medium, the medium further comprises instructions that, when executed by a processor, cause the processor to detect light from the one or more light sources reflected by the cable at the one or more photodetector arrays, and determine, based on the detected light reflected by the cable, whether a change in velocity of the acoustic waves has occurred in the cable.

In one or more aspects of the disclosed computer-readable medium, the instructions that cause the processor to determine whether a change in velocity of the acoustic waves has occurred in the cable are further operable to cause the processor to determine whether a change in a propagation velocity of the acoustic waves has occurred.

In one or more aspects of the disclosed computer-readable medium, the instructions that cause the processor to determine whether a change in velocity of the acoustic waves has occurred in the cable are further operable to cause the processor to determine a propagation time for a wavelength of the acoustic waves.

In one or more aspects of the disclosed computer-readable medium, the instructions that cause the processor to direct light from the one or more light sources toward the cable are further operable to cause the processor to collimate the light from the one or more light sources and direct the collimated light toward the cable.

In one or more aspects of the disclosed computer-readable medium, the acoustic waves comprise one or more axial vibrational modes.

In one or more aspects of the disclosed computer-readable medium, the instructions that cause the processor to determine whether a change in velocity of the acoustic waves has occurred in the cable are further operable to cause the processor to determine a phase velocity of the acoustic waves and determine an elastic modulus of the cable using the determined phase velocity.

In one or more aspects of the disclosed computer-readable medium, the instructions that cause the processor to determine whether a change in velocity of the acoustic waves has occurred in the cable are further operable to cause the processor to determine whether a change in a phase velocity of the acoustic waves has occurred.

In one or more aspects of the disclosed computer-readable medium, the instructions that cause the processor to determine whether a change in velocity of the acoustic waves has occurred in the cable are further operable to cause the processor to determine a wavelength of the acoustic waves.

In one or more aspects of the disclosed computer-readable medium, the instructions that cause the processor to direct light from the one or more light sources toward the cable are further operable to cause the processor to focus the light from the one or more light sources onto the cable.

Illustrative embodiments of the present disclosure have been described herein. In the interest of clarity, not all features of an actual implementation may have been described in this specification. It will of course be appreciated that in the development of any such actual embodiment, numerous implementation-specific decisions may be made to achieve the specific implementation goals, which may vary from one implementation to another. Moreover, it will be appreciated that such a development effort might be complex and time-consuming, but would nevertheless be a routine undertaking for those of ordinary skill in the art having the benefit of the present disclosure.

It will be understood that the terms "couple" or "couples" as used herein are intended to mean either an indirect or a direct connection. Thus, if a first device couples to a second device, that connection may be through a direct connection, or through an indirect electrical or mechanical connection via other devices and connections. It will also be understood that the terms "drilling equipment" and "drilling system" are not intended to limit the use of the equipment and processes described with those terms to drilling an oil well. The terms will also be understood to encompass drilling natural gas wells or hydrocarbon wells in general. Further, such wells can be used for production, monitoring, or injection in relation to the recovery of hydrocarbons or other materials from the subsurface. This could also include geothermal wells intended to provide a source of heat energy instead of hydrocarbons.

To facilitate a better understanding of the present disclosure, examples of certain embodiments have been given. In no way should the examples be read to limit, or define, the scope of the disclosure. Embodiments of the present disclosure may be applicable to horizontal, vertical, deviated, multilateral, u-tube connection, intersection, bypass (drill around a mid-depth stuck fish and back into the wellbore below), or otherwise nonlinear wellbores in any type of subterranean formation. Certain embodiments may be applicable, for example, to logging data acquired with wireline, slickline, and logging while drilling/measurement while drilling (LWD/MWD). Certain embodiments may be applicable to subsea and/or deep sea wellbores. Embodiments described above with respect to one implementation are not intended to be limiting.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Also, the terms in the claims have their plain, ordinary meaning unless otherwise explicitly and clearly defined by the patentee.

What is claimed is:

1. A cable fatigue monitoring system, comprising:
a thermal source;
one or more light sources;
one or more photodetector arrays; and
a computing system comprising a processor, a memory, and a cable distortion module, the cable distortion module operable to:
generate acoustic waves in a cable using the thermal source;
direct light from the one or more light sources toward the cable;
detect light from the one or more light sources transmitted past the cable at the one or more photodetector arrays; and
determine, based on the detected light transmitted past the cable, whether a change in velocity of the acoustic waves has occurred in the cable.

2. The system of claim 1, wherein the acoustic waves comprise one or more circumferential vibrational modes.

3. The system of claim 1, wherein the acoustic waves comprise a carrier frequency between five kilohertz and twenty five kilohertz.

4. The system of claim 1, wherein the cable distortion module is further operable to:
detect light from the one or more light sources reflected by the cable at the one or more photodetector arrays; and
determine, based on the detected light reflected by the cable, whether a change in velocity of the acoustic waves has occurred in the cable.

5. The system of claim 4, wherein the acoustic waves comprise one or more axial vibrational modes.

6. The system of claim 1, wherein the cable distortion module operable to determine whether a change in velocity of the acoustic waves has occurred in the cable is further operable to determine whether a change in a propagation velocity of the acoustic waves has occurred.

7. The system of claim 1, wherein the cable distortion module operable to determine whether a change in velocity of the acoustic waves has occurred in the cable is further operable to determine a propagation time for a wavelength of the acoustic waves.

8. The system of claim 1, wherein the cable distortion module operable to direct light from the one or more light sources toward the cable is further operable to collimate the light from the one or more light sources and direct the collimated light toward the cable.

9. The system of claim 1, wherein the cable distortion module operable to direct light from the one or more light sources toward the cable is further operable to direct light toward the cable in one axis.

10. The system of claim 1, wherein the cable distortion module operable to direct light from the one or more light sources toward the cable is further operable to direct light toward the cable in a plurality of axes.

11. The system of claim 4, wherein the cable distortion module operable to determine whether a change in velocity of the acoustic waves has occurred in the cable is further operable to determine a phase velocity of the acoustic waves and determine an elastic modulus of the cable using the determined phase velocity.

12. The system of claim 4, wherein the cable distortion module operable to determine whether a change in velocity of the acoustic waves has occurred in the cable is further operable to determine whether a change in a phase velocity of the acoustic waves has occurred.

13. The system of claim 4, wherein the cable distortion module operable to determine whether a change in velocity of the acoustic waves has occurred in the cable is further operable to determine a wavelength of the acoustic waves.

14. The system of claim 4, wherein the cable distortion module operable to direct light from the one or more light sources toward the cable is further operable to focus the light from the one or more light sources onto the cable.

15. A method, comprising:
generating acoustic waves in a cable using a thermal source;
directing light from one or more light sources toward the cable;
detecting light from the one or more light sources transmitted past the cable at one or more photodetector arrays; and
determining, based on the detected light transmitted past the cable, that a change in velocity of the acoustic waves has occurred in the cable.

16. The method of claim 15, wherein the acoustic waves comprise one or more circumferential vibrational modes.

17. The method of claim 15, wherein the acoustic waves comprise a carrier frequency between five kilohertz and twenty five kilohertz.

18. The method of claim 15, further comprising:
detecting light from the one or more light sources reflected by the cable at the one or more photodetector arrays; and
determining, based on the detected light reflected by the cable, that a change in velocity of the acoustic waves has occurred in the cable.

19. The method of claim 18, wherein the acoustic waves comprise one or more axial vibrational modes.

20. The method of claim 15, wherein determining whether a change in velocity of the acoustic waves has occurred in the cable further comprises determining whether a change in a propagation velocity of the acoustic waves has occurred.

21. The method of claim 15, wherein determining whether a change in velocity of the acoustic waves has occurred in the cable further comprises determining a propagation time for a wavelength of the acoustic waves.

22. The method of claim 15, wherein directing light from the one or more light sources toward the cable further comprises collimating the light from the one or more light sources and directing the collimated light toward the cable.

23. The method of claim 15, wherein directing light from the one or more light sources toward the cable further comprises directing light toward the cable in one axis.

24. The method of claim 15, wherein directing light from the one or more light sources toward the cable further comprises directing light toward the cable in a plurality of axes.

25. The method of claim 18, wherein determining whether a change in velocity of the acoustic waves has occurred in the cable further comprises determining a phase velocity of the acoustic waves and determining an elastic modulus of the cable using the determined phase velocity.

26. The method of claim 18, wherein determining whether a change in velocity of the acoustic waves has occurred in the cable further comprises determining whether a change in a phase velocity of the acoustic waves has occurred.

27. The method of claim 18, wherein determining whether a change in velocity of the acoustic waves has occurred in the cable further comprises determining a wavelength of the acoustic waves.

28. The method of claim 18, wherein directing light from the one or more light sources toward the cable further comprises focusing the light from the one or more light sources onto the cable.

29. A computer-readable medium comprising instructions that, when executed by a processor, cause the processor to:
generate acoustic waves in a cable using a thermal source;
direct light from one or more light sources toward a cable;
detect light from the one or more light sources transmitted past the cable at one or more photodetector arrays; and
determine, based on the detected light transmitted past the cable, whether a change in velocity of the acoustic waves has occurred in the cable.

30. The computer-readable medium of claim 29, wherein the acoustic waves comprise one or more circumferential vibrational modes.

31. The computer-readable medium of claim 29, wherein the acoustic waves comprise a carrier frequency between five kilohertz and twenty five kilohertz.

32. The computer-readable medium of claim 29, further comprising instructions that, when executed by a processor, cause the processor to:
detect light from the one or more light sources reflected by the cable at the one or more photodetector arrays; and
determine, based on the detected light reflected by the cable, whether a change in velocity of the acoustic waves has occurred in the cable.

33. The computer-readable medium of claim 32, wherein the acoustic waves comprise one or more axial vibrational modes.

34. The computer-readable medium of claim 29, wherein the instructions that cause the processor to determine whether a change in velocity of the acoustic waves has occurred in the cable are further operable to cause the processor to determine whether a change in a propagation velocity of the acoustic waves has occurred.

35. The computer-readable medium of claim 29, wherein the instructions that cause the processor to determine whether a change in velocity of the acoustic waves has occurred in the cable are further operable to cause the processor to determine a propagation time for a wavelength of the acoustic waves.

36. The computer-readable medium of claim 29, wherein the instructions that cause the processor to direct light from the one or more light sources toward the cable are further operable to cause the processor to collimate the light from the one or more light sources and direct the collimated light toward the cable.

37. The computer-readable medium of claim 29, wherein the instructions that cause the processor to direct light from the one or more light sources toward the cable are further operable to direct light toward the cable in one axis.

38. The computer-readable medium of claim 29, wherein the instructions that cause the processor to direct light from the one or more light sources toward the cable are further operable to direct light toward the cable in a plurality of axes.

39. The computer-readable medium of claim 32, wherein the instructions that cause the processor to determine whether a change in velocity of the acoustic waves has occurred in the cable are further operable to cause the processor to determine a phase velocity of the acoustic waves and determine an elastic modulus of the cable using the determined phase velocity.

40. The computer-readable medium of claim 32, wherein the instructions that cause the processor to determine whether a change in velocity of the acoustic waves has occurred in the cable are further operable to cause the processor to determine whether a change in a phase velocity of the acoustic waves has occurred.

41. The computer-readable medium of claim 32, wherein the instructions that cause the processor to determine whether a change in velocity of the acoustic waves has occurred in the cable are further operable to cause the processor to determine a wavelength of the acoustic waves.

42. The computer-readable medium of claim 32, wherein the instructions that cause the processor to direct light from the one or more light sources toward the cable are further operable to cause the processor to focus the light from the one or more light sources onto the cable.

* * * * *